United States Patent
Speckbacher et al.

(10) Patent No.: US 7,500,994 B2
(45) Date of Patent: Mar. 10, 2009

(54) CATIONIC QUINOXALINE THIAZOLE AZO DYE-CONTAINING COLORANTS

(75) Inventors: Markus Speckbacher, Ascheffenburg (DE); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 11/569,913

(22) PCT Filed: Apr. 4, 2005

(86) PCT No.: PCT/EP2005/003506

§ 371 (c)(1),
(2), (4) Date: Oct. 5, 2007

(87) PCT Pub. No.: WO2005/117816

PCT Pub. Date: Dec. 15, 2005

(65) Prior Publication Data

US 2008/0104771 A1    May 8, 2008

(30) Foreign Application Priority Data

Jun. 4, 2004    (DE) .................. 10 2004 027 426

(51) Int. Cl.
*A61Q 5/10* (2006.01)
(52) U.S. Cl. .................. 8/405; 8/406; 8/407; 8/435; 8/437; 8/454; 8/570; 8/575

(58) Field of Classification Search .................. 8/405, 8/406, 407, 435, 437, 454, 570, 575
See application file for complete search history.

(56) References Cited

FOREIGN PATENT DOCUMENTS

DE    100 29 929    12/2001

OTHER PUBLICATIONS

STIC Search Report dated Aug. 7, 2008.*
Radulescu Cristiana "Pharmacodynamic aspects of cationic dyes derivatives" 2004.*
Radulescu Christaina: "Phar,Acodynamic Aspects of Cationic Dyes Derivatives . . . " Rev. Chim., BD. 54, NR. 12, 2003, pp. 965-968 (in English).
Radulescu Cristiana: "Heteropolysalts of Organic Bases" Rev. Chem., BD. 55, NR. 4, 2004, pp. 269-272 (in English).

* cited by examiner

*Primary Examiner*—Eisa B Elhilo
(74) *Attorney, Agent, or Firm*—Michael J. Striker

(57) ABSTRACT

Colorants for keratin fibers comprising cationic quinoxaline thiazole azo dyes of the general formula (I).

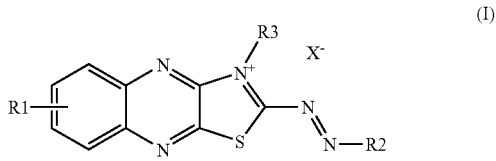

13 Claims, No Drawings

CATIONIC QUINOXALINE THIAZOLE AZO DYE-CONTAINING COLORANTS

CROSS-REFERENCE TO RELATED APPLICATIONS

This application claims priority under 35 U.S.C. 119(a)-(d) to German Patent Application DE 10 2004 027 426.6, filed 4 Jun. 2004

BACKGROUND OF THE INVENTION

1. Field of the Invention

The present invention relates to colorants comprising certain cationic quinoxaline thiazole azo dyes for keratin fibers, such as, for example, hair, wool or furs.

2. Description of Related Art

In general, to color keratin-containing fibers, use is made either of oxidation dyes, which arise as a result of oxidative coupling or one or more developer components with one or more coupler components, or direct dyes. If required, oxidation-stable, direct dyes can be added to the oxidative system in order to achieve particular color effects. Direct dyes are incorporated into suitable carrier masses in order then to be applied to the fibers. This method, generally known as tinting, is easy to use, exceptionally mild and is characterized by low damage to the keratin fibers since no ammonia or peroxide is added. However, the dyes used here have to satisfy a number of requirements. For example, they have to be acceptable from a toxicological and dermatological point of view and allow colorations to be achieved in a desired intensity and brilliance. Furthermore, the colorations achieved also have to have good fastness to light and resistance to shampoos or hair care products, and good fastness to rubbing.

For a direct, nonoxidative colorant for keratin fibers, a combination of different nonoxidative dyes is generally required in order to achieve certain nuances.

Since the choice of such dyes which adequately satisfy the specified requirements is limited, there continues to be a great need for such dyes.

A further, very interesting field of use for direct dyes is their use in products for simultaneous lightening and coloring. In the case of these colorants, which may have a higher content of oxidizing agents, even further-reaching requirements are placed on the dyes used, particularly with regard to adequate resistance to the oxidizing agents used.

To date, there are hardly any dyes which satisfy the above-mentioned prerequisites in every respect and at the same time produce a satisfactory color result. It is therefore an object of the present invention to provide direct dyes for coloring keratin fibers, in particular human hair, which satisfy these requirements.

BRIEF SUMMARY OF THE INVENTION

Surprisingly, it has now been found that cationic quinoxaline thiazole azo dyes of the general formula (I) can be very gently applied to keratin fibers as direct dyes in coloring masses without the addition of an oxidizing agent. Since these dyes are stable to oxidizing agents, they can, however, also be used in lightening colorants comprising oxidizing agents, for example peroxides.

DETAILED DESCRIPTION OF THE INVENTION

The present invention therefore provides
(a) an agent for the nonoxidative coloring of keratin fibers, in particular human hair,
(b) an agent with a simultaneous lightening and coloring of keratin fibers which, besides the dye of the formula (I), comprises an oxidizing agent, and
(c) an oxidative colorant for keratin fibers based on at least one oxidation dye precursor, where the agents (a), (b) and (c) are characterized in that they each comprise at least one cationic quinoxaline thiazole azo dye of the general formula (I),

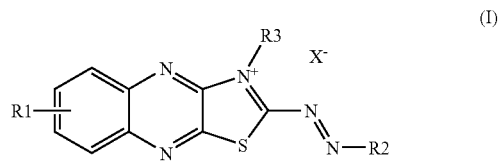

(I)

in which
R1 is a hydrogen atom, an amino group, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group or a carboxylic acid group (—COOH);
R2 is a group of the general formulae (II) to (VI),

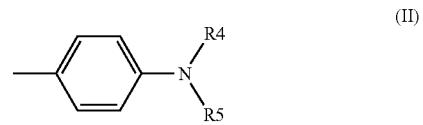

(II)

(III)

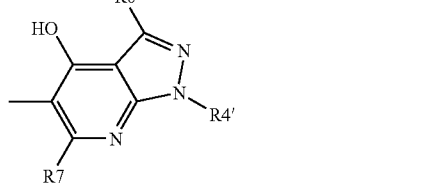

(IV)

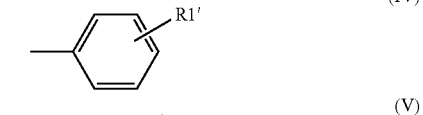

(V)

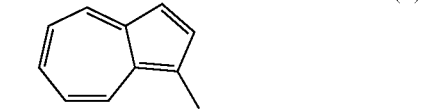

(VI)

where R1' is a hydrogen atom, an amino group, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group or a carboxylic acid group (—COOH);

R4' is hydrogen, a $C_1$-$C_6$-alkylamino group, a $C_1$-$C_6$-N,N-dialkylamino group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group or a phenyl group;

R4 and R5, independently of one another, are hydrogen, a $C_1$-$C_6$-alkylamino group, a $C_1$-$C_6$-N,N-dialkylamino group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group or a phenyl group, or R4 and R5, together with the nitrogen atom to which they are bonded, form a saturated, unsaturated or aromatic heterocycle with at least four ring members (preferably a 4- to 6-membered ring); and R6 and R7, independently of one another, are hydrogen, an amino group, a $C_1$-$C_6$-alkylamino group, a $C_1$-$C_6$-N,N-dialkylamino group, a $C_1$-$C_6$-N,N-(dihydroxyalkyl)amino group, fluorine, chlorine, bromine, iodine, a cyano group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-hydroxyalkyloxy group, a $C_1$-$C_6$-alkyl-carboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group, a phenyl group or a sulfonic acid group;

R3 is a $C_1$-$C_6$-alkyl group, a $C_2$-$C_4$-hydroxyalkyl group or a $c_4$-$C_6$-polyhydroxyalkyl group; where the alkyl groups may in each case be branched or linear, and $X^-$ is an anion, preferably a sulfate anion, a phosphate anion, a hydrogen phosphate anion, an oxalate anion, a formate anion, an acetate anion, a citrate anion, a tartrate anion, a malonate anion, a pyruvate anion, an iodide anion, a chloride anion, a bromide anion or a methylsulfate anion, where the chloride anion, bromide anion and the methylsulfate anion are particularly preferred.

Suitable cationic quinoxaline thiazole azo dyes of the general formula (I) which may be mentioned are, for example: 6-carboxy-2-{(E)-[4-(diethylamino)phenyl]azo}-3-methyl[1,3]thiazolo[4,5-b]quinoxalin-3-ium methylsulfate, 6-carboxy-2-((E)-{4-[(2-hydroxyethyl)amino]-phenyl}azo)-3-methyl[1,3]thiazolo[4,5-b]quinoxalin-3-ium methylsulfate, 2-((E)-{4-[bis(2-hydroxyethyl)-amino]phenyl}azo)-6-carboxy-3-methyl[1,3]thiazolo[4,5-b]quinoxalin-3-ium methylsulfate, 6-carboxy-2-((E)-{4-[(2-hydroxyethyl)(methyl) amino]phenyl}azo)-3-methyl-[1,3]thiazolo[4,5-b] quinoxalin-3-ium methylsulfate, 6-carboxy-2-((E)-{4-[ethyl (2-hydroxyethyl)amino]phenyl}-azo)-3-methyl[1,3]thiazolo [4,5-b]quinoxalin-3-ium methylsulfate, 6-carboxy-2-((E)-{4-[cyano(ethyl)amino]-phenyl}azo)-3-methyl[1,3]thiazolo [4,5-b]quinoxalin-3-ium methylsulfate, 6-nitro-2-{(E)-[4-(diethylamino)-phenyl]azo}-3-methyl[1,3]thiazolo[4,5-b] quinoxalin-3-ium methylsulfate, 6-methoxy-2-((E)-{4-[(2-hydroxyethyl)amino]phenyl}azo)-3-methyl[1,3]thiazolo[4,5-b]quinoxalin-3-ium methylsulfate, 6-hydroxy-2-((E)-{4-[bis(2-hydroxyethyl)amino]phenyl}azo)-6-carboxy-3-methyl[1,3]thiazolo[4,5-b]quinoxalin-3-ium methylsulfate, 6-nitro-2-((E)-{4-[(2-hydroxyethyl)-(methyl)amino] phenyl}azo)-3-methyl[1,3]thiazolo[4,5-b]quinoxalin-3-ium methylsulfate, 6-methoxy-2-((E)-{4-[ethyl(2-hydroxyethyl) amino]phenyl}azo)-3-methyl[1,3]-thiazolo [4,5-b]quinoxalin-3-ium methylsulfate and 6-carboxy-2-{(E) [4-(dimethylamino)phenyl]azo}-3-methyl-[1,3]thiazolo[4,5-b] quinoxalin-3-ium methylsulfate.

Preferred compounds of the general formula (I) are 6-carboxy-2-{(E)-[4-(diethylamino)phenyl]azo}-3-methyl-[1,3] thiazolo[4,5-b]quinoxalin-3-ium methylsulfate, 6-carboxy-2-((E)-{4-[(2-hydroxyethyl)amino]phenyl}azo)-3-methyl[1, 3]thiazolo[4,5-b]quinoxalin-3-ium methylsulfate, 2-((E)-{4-[bis(2-hydroxyethyl)amino]phenyl}-azo)-6-carboxy-3-methyl[1,3]thiazolo[4,5-b]quinoxalin-3-ium methylsulfate, 6-carboxy-2-((E)-{4-[(2-hydroxyethyl)(methyl)amino] phenyl}azo)-3-methyl[1,3]thiazolo-[4,5-b]quinoxalin-3-ium methylsulfate, 6-carboxy-2-((E)-{4-[ethyl(2-hydroxyethyl)amino]phenyl}azo) -3-methyl[1,3]thiazolo[4,5-b] quinoxalin-3-ium methylsulfate and 6-carboxy-2-((E)-{4-[cyano(ethyl)amino]-phenyl}azo)-3-methyl[1,3]thiazolo[4, 5-b]quinoxalin-3-ium methylsulfate.

The dye derivatives of the general formula (I) according to the invention are accessible by standard operations from commercially available or easy-to-produce components.

Thus, the quinoxaline thiazole azo dyes of the formula (I) can be prepared by a two-stage synthesis method in which, in a first step, as a result of an azo coupling of 2-aminoquinoxaline thiazoles (e.g. 2-aminothiazolo[5,4-b]quinoxaline-7-carboxylic acid) with activated aromatics, the quinoxaline thiazole azo compounds of the formula (Ia) are prepared (scheme 1) and then, in a second step, by reacting the compounds of the formula (Ia) with suitable alkylating agents (e.g. DMS=dimethyl sulfate), the corresponding cationic quinoxaline thiazole azo dyes of the formula (I) are obtained (scheme 2).

Scheme 1:

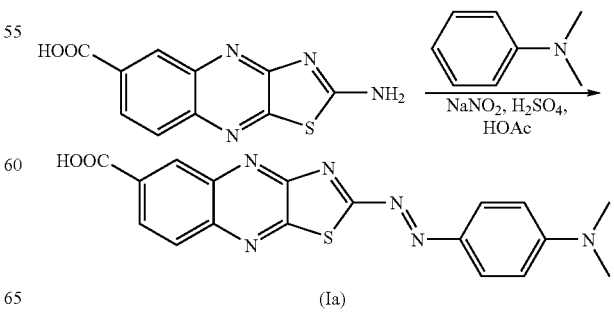

(Ia)

Scheme 2:

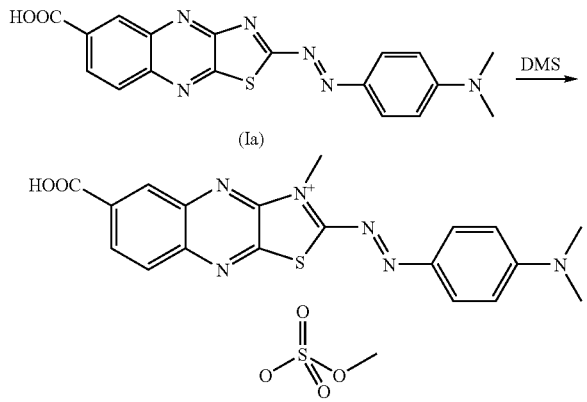

The colorants according to the invention comprising the cationic quinoxaline thiazole azo dyes of the general formula (I) permit an even coloring of keratin fibers, in particular human hair, with good stability towards light, perspiration and shampooing, with intense, brilliant colorations being obtained even under gentle conditions.

The cationic quinoxaline thiazole azo dyes of the general formula (I) are present in the colorants according to the invention preferably in a total amount of from 0.01 to 10% by weight, in particular 0.1 to 8% by weight.

Besides the dyes of the general formula (I), the colorant (a) according to the invention can additionally also comprise further known direct dyes from the group consisting of nitro dyes, azo dyes, anthraquinone dyes and triphenylmethane dyes, such as, for example, 1,4-bis[(2-hydroxyethyl)amino]-2-nitrobenzene, 1-(2-hydroxyethyl)amino-2-nitro-4-[di(2-hydroxyethyl)amino]benzene, (HC Blue No. 2), 1-amino-3-methyl-4-[(2-hydroxyethyl)amino]-6-nitrobenzene, (HC Violet No. 1), 4-[ethyl-(2-hydroxyethyl)amino]-1-[(2-hydroxyethyl)amino]-2-nitrobenzene hydrochloride (HC Blue No. 12), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene, (HC Violet No. 2); 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-2-nitro-1-((prop-2-en-1-yl)amino)benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene, (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)-amino]-5-nitrobenzene, (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride, (HC Yellow No. 9), 1-[(2-ureidoethyl)amino]-4-nitrobenzene, 4-[(2,3-dihydroxypropyl)amino]-3-nitro-1-trifluoromethylbenzene, (HC Yellow No. 6), 1-chloro-2,4-bis[(2-hydroxyethyl)amino] -5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene, (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 2,4-dinitro-1-hydroxynaphthalene, 1,4-di[(2,3-dihydroxypropyl)amino]-9,10-anthraquinone, 1,4-di[(2-hydroxyethyl)amino]-9,10-anthraquinone (CI61545, Disperse Blue 23), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl)amino]-9,10-anthraquinone (HC Red No. 8), 1,4-diamino-9,10-anthraquinone (CI61100, Disperse Violet No. 1), 1-amino-4-(methylamino)-9,10-anthraquinone (CI61105, Disperse Violet No. 4, Solvent Violet No. 12), N-(6-((3-chloro-4-(methylamino)phenyl)imino)-4-methyl-3-oxo-1,4-cyclohexadien-1-yl)urea (HC Red No. 9), 2-((4-(di(2-hydroxyethyl)amino)phenyl)amino)-5-((2-hydroxyethyl)amino)-2,5-cyclohexadiene-1,4-dione (HC Green No. 1), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis(dicyanomethylene)-indane, di[4-(diethylamino)phenyl][4-(ethylamino)-naphthyl]carbenium chloride (CI42595; Basic Blue No. 7), di[4-(dimethylamino)phenyl][4-(phenylamino)-naphthyl] carbenium chloride (CI44045; Basic Blue No. 26), Basic Blue No. 77, 8-amino-2-bromo-5-hydroxy-4-imino-6-[(3-(trimethylammonio)phenyl)amino]-1(4H)-naphthalinone chloride (CI56059; Basic Blue No. 99), tri(4-amino-3-methylphenyl)carbenium chloride (CI42520; Basic Violet No. 2), di(4-aminophenyl)(4-amino-3-methylphenyl)carbenium chloride (CI42510; Basic Violet No. 14), 1-[(4-aminophenyl)azo]-7-(trimethylammonio)-2-naphthol chloride (CI12250; Basic Brown No. 16), 3-[(4-amino-2,5-dimethoxyphenyl)azo]-N,N,N-trimethylbenzenaminium chloride (CI112605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI12251; Basic Brown No. 17), 2-((4-aminophenyl)azo)-1,3-dimethyl-1H-imidazol-3-ium chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)azo-1H-imidazol-3-ium chloride (Basic Red No. 51), 2-hydroxy-1-[(2-methoxyphenyl)azo]-7-(trimethylammonio)naphthalene chloride (CI12245;

Basic Red No. 76), 3-methyl-1-phenyl-4-[(3-(trimethylammonio)phenyl)azo]pyrazol-5-one chloride (CI12719; Basic Yellow No. 57), 1-methyl-4-((methylphenylhydrazono)methyl)pyridinium methylsulfate (Basic Yellow No. 87), 1-(2-morpholiniumpropylamino)-4-hydroxy-9,10-anthraquinone methylsulfate, 1-[(3-(dimethylpropylaminium)propyl)-amino]-4-(methylamino)-9,10-anthraquinone chloride, 1-[di(2-hydroxyethyl)amino]-3-methyl-4-[(4-nitrophenyl)azo] benzene (CI11210, Disperse Red No. 17), 1-[di(2-hydroxyethyl)amino]-4-[(4-nitrophenyl)azo]benzene, (Disperse Black No. 9), 4-[(4-aminophenyl)azo]-1-[di(2-hydroxyethyl)amino]-3-methylbenzene, (HC Yellow No. 7), 2,6-diamino-3-[(pyridin-3-yl)azo]pyridine and 2-((4-(ethyl (2-hydroxyethyl)amino)-2-methylphenyl)azo)-5-nitro-1,3-thiazole (CI111935; Disperse Blue No. 106), alone or in a mixture with one another.

The colorant (b) according to the invention, which is characterized by a content of an oxidizing agent, preferably hydrogen peroxide or its addition compounds onto urea, melamine, sodium borate or sodium carbonate, and in particular hydrogen peroxide can, besides the dyes of the general formula, additionally also comprise further oxidation-stable direct dyes, such as, for example, 3-(2',6'-diaminopyridyl-3'-azo)pyridine (=2,6-diamino-3-((pyridin-3-yl)azo)pyridine, 2-((4-(ethyl(2-hydroxyethyl)amino)-2-methylphenyl)azo-5-nitro-1,3-thiazole (Disperse Blue 106), N,N-di(2-hydroxyethyl)-3-methyl-4-((4-nitrophenyl)azo)aniline (Disperse Red 17, CI 11210), 3-diethylamino-7-(4-dimethylaminophenylazo)-5-phenylphenazinium chloride (CI 11050), 4-(2-thiazolylazo)resorcinol, 4-((4-phenylamino)azo)benzosulfonic acid sodium salt (Orange IV), 1-((3-aminopropyl)amino)-9,10-anthracenedione (HC Red No. 8), 3',3",4,5,5',5",6,7-octabromophenol sulfonephthalein (Tetrabromophenol Blue), 1-((4-amino-3,5-dimethylphenyl)-(2,6-dichlorophenyl)methylene)-3,5-dimethyl-4-imino-2,5-cyclohexadiene phosphoric acid (1:1) (Basic Blue 77), 3',3",5', 5 "-tetrabromo-m-cresol sulfonephthalein, 2,4-dinitro-1-naphthol-7-sulfonic acid disodium salt (Acid Yellow 1, CI 10316), 4-[2'-hydroxy-1'-naphthyl)azo]benzosulfonic acid sodium salt (Acid Orange 7, CI 15510), 3',6'-dihydroxy-2',4',5',7'-tetraiodospiro[isobenzofuran-1(3H), 9' (9H)-xanthen]-3-one disodium salt (Acid Red 51, CI 45430), 6-hydroxy-5-((2-methoxy-5-methyl-4-sulfophenyl)azo)-2-naphthalenesulfonic acid disodium salt (FD&C Red 40, CI 16035), 2,4-dinitro-1-naphthol sodium salt (Acid Yellow 24; CI 10315), 2',4',5',7'-tetrabromo-4,5,6,7-tetrachloro-3',6'-dihydroxyspiro(isobenzofuran-1(3H), 9'[9H]xanthen]-3-one disodium salt (Acid Red 92; CI 45410), 4-(2-hydroxy-1-naphthylazo)-3-methylbenzenesulfonic acid sodium salt (Acid Orange 8, CI 15575), 2-amino-1,4-naphthalenedione, dithizone (1,5-diphenylthiocarbazone), N-(2-hydroxyethyl)-(2-nitro-4-trifluoromethyl)aniline (HC Yellow 13), N-(2-hydroxyethyl)-4-nitroaniline and 4-chloro-N-(2,3-dihydroxypropyl)-2-nitroaniline.

The abovementioned direct dyes may be present in a total amount of from about 0.01 to 4% by weight, where the total content of dyes in the colorant according to the invention is preferably about 0.01 to 10% by weight, in particular 0.1 to 5% by weight. Besides the dyes of the general formula (I), the oxidation colorant (c) according to the invention, which is mixed prior to use with an oxidizing agent (in particular hydrogen peroxide or its addition compounds), additionally comprises oxidation dye precursors. Suitable oxidation dye precursors which may be specified are, for example, the following developer substances and coupler substances and self-coupling compounds:

(i) Developer substances: 1,4-diaminobenzene (p-phenylenediamine), 1,4-diamino-2-methylbenzene (p-tolylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-(2-(acetylamino)ethoxy)-1,4-diaminobenzene, 4-phenylaminoaniline, 4-dimethylaminoaniline, 4-diethylaminoaniline, 4-dipropylaminoaniline, 4-[ethyl(2-hydroxyethyl)amino]aniline, 4-[di(2-hydroxyethyl)amino]aniline, 4-[di(2-hydroxyethyl)amino]-2-methylaniline, 4-[(2-methoxyethyl)-amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl)benzene, 1,3-bis[(4-aminophenyl)(2-hydroxyethyl)amino]-2-propanol, 1,4-bis[(4-aminophenyl)amino]butane, 1,8-bis(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol, alone or in a mixture with one another.

(ii) Coupler substances: N-(3-dimethylaminophenyl)urea, 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)-benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)-amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)-ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolenedione, alone or in a mixture with one another.

(iii) Self-coupling compounds: 2-amino-5-methylphenol, 2-amino-6-methylphenol, 2-amino-5-ethoxyphenol or 2-propylamino-5-aminopyridine.

The total amount of the oxidation dye precursors present in the colorant (c) according to the invention is about 0.01 to 12% by weight, in particular about 0.2 to 6% by weight.

The colorant (a), (b) or (c) according to the invention can also comprise all additives which are customary and known for such preparations, for example perfume oils, complexing agents, waxes, preservatives, thickeners, antioxidants, alginates, guar gum, hair care substances, such as, for example, cationic polymers or lanoline derivatives, or anionic, nonionic, amphoteric or cationic surface-active substances. Preference is given to using amphoteric or nonionic surface-active substances, for example betaine surfactants, propionates and glycinates, such as, for example, cocoamphoglycinates or cocoamphodiglacinates, ethoxylated surfactants with 1 to 1000 ethylene oxide units, preferably with 1 to 300 ethylene oxide units, such as, for example, glyceride alkoxylates, for example castor oil ethoxylated with 25 ethylene oxide units, polyglycolamides, ethoxylated alcohols and ethoxylated fatty alcohols (fatty alcohol alkoxylates) and ethoxylated fatty acid sugar esters, in particular ethoxylated sorbitan fatty acid esters. The abovementioned constituents are used in the amounts customary for such purposes, for example the surface-active substances in a concentration of from 0.1 to 30% by weight, and the care substances in an amount of from 0.1 to 5% by weight.

The colorant (a), (b) or (c) according to the invention can, particularly if it is a hair colorant, be in the form of a powder or granules, which are dissolved prior to use in an aqueous or aqueous-alcoholic preparation, or else in the form of an aqueous or aqueous-alcoholic solution, a cream, a gel, an emulsion or an aerosol foam, where the hair colorant can be formulated either in the form of a single-component preparation, or in the form of a multicomponent preparation, for example in the form of a two-component preparation in which the respective dye derivative of the general formulae (I) and (II) is packaged separately from the other constituents and the ready-to-use hair colorant is only prepared directly prior to use by mixing the two components.

The colorant (a), (b) or (c) according to the invention generally has a pH of from about 2 to 11, preferably about 5 to 10, and in particular a neutral to basic pH of from about 7 to 10. To establish the pH according to the invention, either organic or inorganic acids or bases are suitable. Suitable acids to be mentioned are, in particular, the following acids: α-hydroxycarboxylic acids, such as, for example, glycolic acid, lactic acid, tartaric acid, citric acid or malic acid, ascorbic acid, gluconolactone, acetic acid, hydrochloric acid or phosphoric acid, and mixtures of these acids. Suitable bases to be mentioned are, in particular, sodium carbonate, sodium hydrogencarbonate, alkanolamines, for example monoethanolamine or triethanolamine, ammonia, aminomethylpropanol and sodium hydroxide, and mixtures thereof.

Depending on the intended use, the colorant according to the invention can be used with one or more oxidizing agents (lightening; oxidation colorants) or without an oxidizing agent (nonoxidative colorants). The colorant according to the invention is usually used by applying to the hair an amount of the hair colorant sufficient for coloring the hair, about 30 to 120 grams depending on the length of the hair, the hair colorant is left to act at about 15 to 45 degrees Celsius for about 1 to 60 minutes, preferably from 5 to 30 minutes, the hair is then thoroughly rinsed with water, optionally washed with a shampoo and/or after-treated with a hair conditioner and finally dried.

If required, the agent is mixed with an oxidizing agent prior to use.

If no oxidizing agents are added to the coloring mass, the colorant described above can also comprise natural or synthetic polymers customary for cosmetic compositions, or modified polymers of natural origin, as a result of which setting of the hair is achieved at the same time as the coloring. Such agents are generally referred to as setting tints or setting colors. Of the synthetic polymers known for this purpose in cosmetics, mention may be made, for example, of polyvinylpyrrolidone, polyvinyl acetate, polyvinyl alcohol or polyacrylic compounds, such as polyacrylic acid or polymethacrylic acid, basic polymers of esters of polyacrylic acid, polymethylacrylic acid and amino alcohols, for example their salts or quaternization products, polyacrylonitrile, polyvinyl acetates, and copolymers of such compounds, such as, for example, polyvinylpyrrolidone-vinyl acetate; whereas natural polymers or modified natural polymers which may be used are, for example, chitosan (deacetylated chitin) or chitosan derivatives. The abovementioned polymers may be present in the colorant according to the invention (a) in the amounts customary for such agents, in particular in an amount of from about 1 to 5% by weight. The pH of the setting tint or setting color according to the invention is preferably about 6 to 9.

The hair colorant with additional setting is used in a known and customary manner by wetting the hair with the setting agent, fixing (arranging) the hair in the hairstyle and then drying it.

The colorants (a), (b) and (c) according to the invention permit an even, intense and permanent coloration of keratin fibers (for example human hair, wool or furs) without appreciable staining of the skin or scalp, where this coloration endures five and more hair washes, even in the case of colorant (a), without notable fading of the hair color.

The examples below are intended to illustrate the subject matter of the invention in more detail without limiting it thereto.

EXAMPLES

Example 1

Hair Colorant Without Oxidizing Agent

| | | |
|---|---|---|
| 2.5 | mmol | Dye according to general formula (I) |
| 5.0 | g | Ethanol |
| 4.0 | g | Decylpolyglucose |
| 0.2 | g | Ethylenediaminotetraacetic acid disodium salt hydrate |
| ad 100 | g | Water, demineralized |

The coloring solution is adjusted to a pH of from 7 to 10 by adding ammonia.

Hair coloring is carried out by applying to the hair an amount of the colorant sufficient for coloring the hair and, after a contact time of 30 minutes at 40° C., the hair is rinsed with lukewarm water and finally dried.

The coloring results are summarized in Table 1 below.

TABLE 1

| Dye of the general formula (I) | Color |
|---|---|
| 6-Carboxy-2-{(E)-[4-(diethylamino)phenyl]azo}-3-methyl[1,3]thiazolo[4,5-b]quinoxalin-3-ium methylsulfate | Blue-violet |
| 2-((E)-{4-[bis(2-hydroxyethyl)amino]phenyl}-azo)-6-carboxy-3-methyl[1,3]thiazolo[4,5-b]quinoxalin-3-ium methylsulfate | Blue |

Example 2

Hair Coloring for Simultaneous Lightening and Coloring (with Oxidizing Agent)

| | | |
|---|---|---|
| 2.5 | mmol | 6-Carboxy-2-((E)-{4-[ethyl(2-hydroxyethyl)-amino]phenyl}azo)-3-methyl[1,3]thiazolo[4,5-b]quinoxalin-3-ium methylsulfate |
| 5.0 | g | Ethanol |
| 4.0 | g | Decylpolyglucose |
| 0.2 | g | Ethylenediaminotetraacetic acid disodium salt hydrate |
| ad 100 | g | Water, demineralized |

50 g of the above coloring solution are mixed directly prior to use with 50 g of a 6% strength hydrogen peroxide emulsion to give a homogeneous mass. An amount of this coloring mass sufficient for coloring the hair is then applied to the hair. After a contact time of 45 minutes at 40° C., the hair is rinsed with lukewarm water and treated with an acidic conditioner, rinsed again and dried. A gray-blue color is obtained.

Unless stated otherwise, all of the percentages given in the present application are percentages by weight.

What is claimed is:

1. An agent for the nonoxidative coloring of keratin fibers, comprising from 0.01% to 10% by weight of at least one cationic quinoxaline thiazole azo dye of the general formula (I),

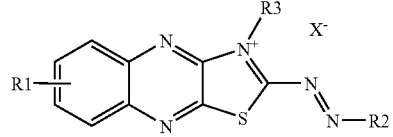

in which

R1 is a hydrogen atom, an amino group, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group or a carboxylic acid group (—COOH);

R2 is a group of the general formulae (II) to (VI),

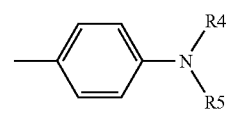

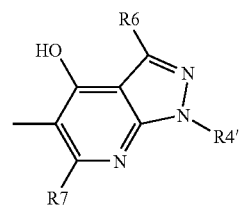

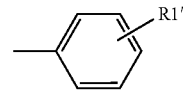

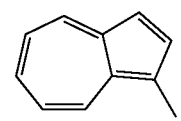

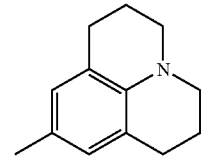

where R1' is a hydrogen atom, an amino group, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group or a carboxylic acid group (—COOH);

R4' is hydrogen, a $C_1$-$C_6$-alkylamino group, a $C_1$-$C_6$-N,N-dialkylamino group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$- hydroxyalkyl group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group or a phenyl group;

R4 and R5, independently of one another, are hydrogen, a $C_1$-$C_6$-alkylamino group, a $C_1$-$C_6$-N,N-dialkylamino group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group or a phenyl group, or R4 and R5, together with the nitrogen atom to which they are bonded, form a saturated, unsaturated or aromatic heterocycle with at least four ring members; and R6 and R7, independently of one another, are hydrogen, an amino group, a $C_1$-$C_6$-alkylamino group, a $C_1$-$C_6$-N,N-dialkylamino group, a $C_1$-$C_6$-N,N-(dihydroxyalkyl)amino group, fluorine, chlorine, bromine, iodine, a cyano group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-hydroxyalkyloxy group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group, a phenyl group or a sulfonic acid group;

R3 is a $C_1$-$C_6$-alkyl group, a $C_2$-$C_4$-hydroxyalkyl group or a $C_4$-$C_6$-polyhydroxyalkyl group;

where the alkyl groups may in each case be branched or linear, and

X— is an anion.

2. The agent as claimed in claim 1, further comprising at least one natural polymer, synthetic polymer or modified polymer of natural origin customary for cosmetic agents, and is in the form of a setting tint or setting color.

3. An agent for the simultaneous lightening and coloring of keratin fibers comprising: (i) an oxidizing agent and (ii) at least one cationic quinoxaline thiazole azo dye of the general formula (I),

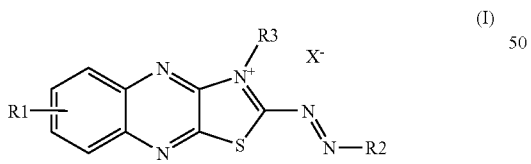

in which

R1 is a hydrogen atom, an amino group, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group or a carboxylic acid group (—COOH);

R2 is a group of the general formulae (II) to (VI),

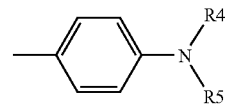

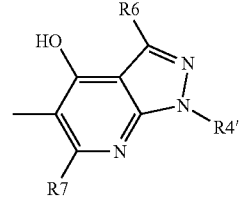

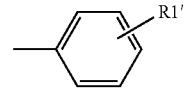

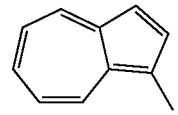

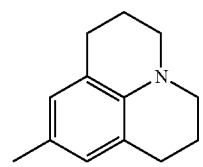

where R1' is a hydrogen atom, an amino group, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group or a carboxylic acid group (—COOH);

R4' is hydrogen, a $C_1$-$C_6$-alkylamino group, a $C_1$-$C_6$-N,N-dialkylamino group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group or a phenyl group;

R4 and R5, independently of one another, are hydrogen, a $C_1$-$C_6$-alkylamino group, a $C_1$-$C_6$-N,N-dialkylamino group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group or a phenyl group, or R4 and R5, together with the nitrogen atom to which they are bonded, form a saturated, unsaturated or aromatic heterocycle with at least four ring members; and R6 and R7, independently of one another, are hydrogen, an amino group, a $C_1$-$C_6$-alkylamino group, a $C_1$-$C_6$-N,N- dialkylamino group, a $C_1$-$C_6$-N,N-(dihydroxyalkyl) amino group, fluorine, chlorine, bromine, iodine, a cyano group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-hydroxyalkyloxy group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group, a phenyl group or a sulfonic acid group;

R3 is a $C_1$-$C_6$-alkyl group, a $C_2$-$C_4$-hydroxyalkyl group or a $C_4$-$C_6$-polyhydroxyalkyl group;

where the alkyl groups may in each case be branched or linear, and

X— is an anion.

4. The agent as claimed in claim 3, wherein the oxidizing agent is chosen from hydrogen peroxide or its addition compounds onto urea, melamine, sodium borate or sodium carbonate.

5. An agent for the oxidative coloring of keratin fibers based on oxidation dye precursors, comprising at least one cationic quinoxaline thiazole azo dye of the general formula (I),

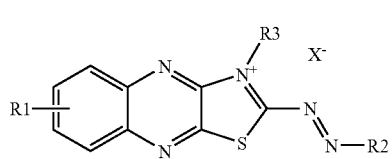
(I)

in which

R1 is a hydrogen atom, an amino group, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group or a carboxylic acid group (—COOH);

R2 is a group of the general formulae (II) to (VI),

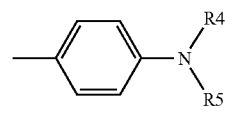
(II)

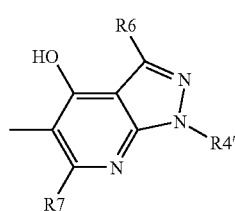
(III)

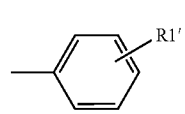
(IV)

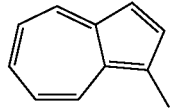
(V)

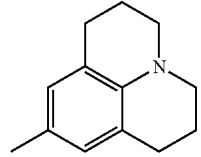
(VI)

where R1' is a hydrogen atom, an amino group, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group or a carboxylic acid group (—COOH);

R4' is hydrogen, a $C_1$-$C_6$-alkylamino group, a $C_1$-$C_6$-N,N-dialkylamino group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group or a phenyl group;

R4 and R5, independently of one another, are hydrogen, a $C_1$-$C_6$-alkylamino group, a $C_1$-$C_6$-N,N-dialkylamino group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group or a phenyl group, or R4 and R5, together with the nitrogen atom to which they are bonded, form a saturated, unsaturated or aromatic heterocycle with at least four ring members; and R6 and R7, independently of one another, are hydrogen, an amino group, a $C_1$-$C_6$-alkylamino group, a $C_1$-$C_6$-N,N-dialkylamino group, a $C_1$-$C_6$-N,N-(dihydroxyalkyl) amino group, fluorine, chlorine, bromine, iodine, a cyano group, a $C_1$-$C_6$-alkylcyano group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-hydroxyalkyloxy group, a $C_1$-$C_6$-alkylcarboxylic acid group, a $C_1$-$C_6$-alkylcarboxylic acid ester group, a $C_1$-$C_6$-alkylcarboxamide group, a $C_1$-$C_6$-alkylsulfonic acid group, a $C_1$-$C_6$-alkylsulfonic acid ester group, a $C_1$-$C_6$-alkylsulfonamide group, a phenyl group or a sulfonic acid group;

R3 is a $C_1$-$C_6$-alkyl group, a $C_2$-$C_4$-hydroxyalkyl group or a $C_4$-$C_6$-polyhydroxyalkyl group;

where the alkyl groups may in each case be branched or linear, and

X— is an anion.

6. The agent as claimed in claim 5, characterized in that it comprises 0.01 to 12% by weight of at least one oxidation dye precursor.

7. The agent as claimed in claim 1, wherein the cationic quinoxaline thiazole azo dye of the general formula (I) is chosen from 6-carboxy-2-{(E)-[4-(diethylamino)phenyl]azo}-3-methyl[1,3]thiazolo[4,5-b]quinoxal-in-3-ium methylsulfate, 6-carboxy-2-((E)-{4-[(2-hydroxyethyl)amino]phenyl}azo)-3-methyl[1,3]thiazolo[4,5-b]quinoxalin-3-ium methylsulfate, 2-((E)-{4-[bis(2-hydroxyethyl)amino]phenyl}azo)-6-carboxy-3-methyl[1,3]thiazolo[4,5-b]quinoxalin-3-ium methylsulfate, 6-carboxy-2-((E)-{4-[(2-hydroxyethyl)(methyl)amino]phenyl}azo)-3-methyl-[1,3]thiazolo[4,5-b]quinoxalin-3-ium methylsulfate, 6-carboxy-2-((E)-{4-[ethyl(2-hydroxyethyl)amino]phenyl}azo)-3-methyl[1,3]thiazolo[4,5-b]quinoxalin-3-ium methylsulfate, 6-carboxy-2-((E)-{4-[cyano(ethyl)amino]phenyl}azo)-3-methyl-[1,3]thiazolo[4,5-b]quinoxalin-3-ium methylsulfate, 6-nitro-2-{(E)-[4-(diethylamino)phenyl]azo}-3-methyl[1,3]thiazolo[4,5-b]quinoxalin-3-ium methylsulfate, 6-methoxy-2-((E)-{4-[(2-hydroxyethyl)amino]phenyl}azo)-3-methyl[1,3]thiazolo[4,5-b]quinoxalin-3-ium methylsulfate, 6-hydroxy-2-((E)-{4-[bis(2-hydroxyethyl)amino]phenyl}azo)-6-carboxy-3-methyl[1,3]thiazolo[4,5-b]quinoxalin-3-ium methylsulfate, 6-nitro-2-((E)-{4-[(2-hydroxyethyl)(methyl)amino]phenyl}azo)-3-methyl-[1,3]thiazolo[4,5-b]quinoxalin-3-ium methylsulfate, 6-methoxy-2-((E)-{4-[ethyl(2-hydroxyethyl)amino]phenyl}azo)-3-methyl[1,3]thiazolo[4,5-b]quinoxalin-3-ium methylsulfate and 6-carboxy-2-{(E)-[4-dimethylamino)phenyl]azo}-3-methyl[1,3]thiazolo[4,5-b]quinoxalin-3-ium methyl-sulfate.

8. The agent as claimed in claim 3, wherein the cationic quinoxaline thiazole azo dye of the general formula (I) is present in a total amount of from 0.01 to 10% by weight.

9. The agent as claimed in claim 1, wherein the agent is a hair colorant.

10. The agent as claimed in claim 3, wherein the cationic quinoxaline thiazole azo dye of the general formula (I) is chosen from 6-carboxy-2-{(E)-[4-(diethylamino)phenyl]azo}-3-methyl[1,3]thiazolo[4,5-b]quinoxal-in-3-ium methylsulfate, 6-carboxy-2-((E)-{4-[(2-hydroxyethyl)amino]phenyl}azo)-3-methyl[1,3]thiazolo[4,5-b]quinoxalin-3-ium methylsulfate, 2-((E)-{4-[bis(2-hydroxyethyl)amino]phenyl}azo)-6-carboxy-3-methyl[1,3]thiazolo[4,5-b]quinoxalin-3-ium methylsulfate, 6-carboxy-2-((E)-{4-[(2-hydroxyethyl)(methyl)amino]phenyl}azo)-3-methyl[1,3]thiazolo[4,5-b]quinoxalin-3-ium methylsulfate, 6-carboxy-2-((E)-{4-[ethyl(2-hydroxyethyl)amino]phenyl}azo)-3-methyl[1,3]thiazolo[4,5-b]quinoxalin-3-ium methylsulfate, 6-carboxy-2-((E)-{4-[cyano(ethyl)amino]phenyl}azo)-3-methyl-[1,3]thiazol[4,5-b]quinoxalin-3-ium methylsulfate, 6-nitro-2-{(E)-[4-(diethylamino)phenyl]azo}-3-methyl[1,3]thiazolo[4,5-b]quinoxalin-3-ium methylsulfate, 6-methoxy-2-((E)-{4-[(2-hydroxyethyl)amino]phenyl}azo)-3-methyl[1,3]thiazolo[4,5-b]quinoxalin-3-ium methylsulfate, 6-hydroxy-2-((E)-{4-[bis(2-hydroxyethyl)amino]phenyl}azo)-6-carboxy-3-methyl[1,3]thiazolo[4,5-b]quinoxalin-3-ium methylsulfate, 6-nitro-2-((E)-{4-[(2-hydroxyethyl)(methyl)amino]phenyl}azo)-3-methyl[1,3]thiazolo[4,5-b]quinoxalin-3-ium methylsulfate, 6-methoxy-2-((E)-{4-[ethyl(2-hydroxyethyl)amino]phenyl}azo)-3-methyl[1,3]thiazolo[4,5-b]quinoxalin-3-ium methylsulfate and 6-carboxy-2-{(E)-[4-(dimethylamino)phenyl]azo}-3-methyl[1,3]thiazolo[4,5-b]quinoxalin-3-ium methyl-sulfate.

11. The agent as claimed in claim 1, wherein the anion $X^-$ is selected from the group consisting of: a sulfate anion, a phosphate anion, a hydrogen phosphate anion, an oxalate anion, a formate anion, an acetate anion, a citrate anion, a tartrate anion, a malonate anion, a pyruvate anion, an iodide anion, a chloride anion, a bromide anion, and a methylsulfate anion.

12. The agent as claimed in claim 3, wherein the anion $X^-$ is selected from the group consisting of: a sulfate anion, a phosphate anion, a hydrogen phosphate anion, an oxalate anion, a formate anion, an acetate anion, a citrate anion, a tartrate anion, a malonate anion, a pyruvate anion, an iodide anion, a chloride anion, a bromide anion, and a methylsulfate anion.

13. The agent as claimed in claim 5, wherein the anion $X^-$ is selected from the group consisting of: a sulfate anion, a phosphate anion, a hydrogen phosphate anion, an oxalate anion, a formate anion, an acetate anion, a citrate anion, a tartrate anion, a malonate anion, a pyruvate anion, an iodide anion, a chloride anion, a bromide anion, and a methylsulfate anion.

* * * * *